US00PP09541P

United States Patent [19]

Surkijn

[11] Patent Number: Plant 9,541

[45] Date of Patent: May 7, 1996

[54] APPLE TREE 'ROMAGOLD'

[76] Inventor: Romain Surkijn, Betserbaan 56, B-3545, Halen, Belgium

[21] Appl. No.: 307,389

[22] Filed: Sep. 15, 1994

Related U.S. Application Data

[63] Continuation of Ser. No. 13,021, Feb. 2, 1993, abandoned.

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

| | | | |
|---|---|---|---|
| P.P. 5,937 | 4/1987 | Moren-De Coster | Plt./34.1 |
| P.P. 6,148 | 4/1988 | Ligonniere | Plt./34.1 |
| P.P. 7,146 | 2/1990 | Schneica | Plt./34.1 |
| P.P. 7,590 | 7/1991 | Lichtenauer | Plt./34.1 |
| P.P. 8,049 | 12/1992 | Swillen | Plt./34.1 |

OTHER PUBLICATIONS

Goddrie, P. D., et al., (1990) *Jonagold Color Varieties,* Brochure, Fruit Cultivation Test Station, Wilhelminadorp (with English Translation).

*Primary Examiner*—James R. Feyrer
*Attorney, Agent, or Firm*—Stratton Ballew

[57] ABSTRACT

A new variety of apple originating as a spontaneous limb mutation of its parent vairety Jonagold (unpatented) and unique particularly for its over-all, early, broadly striped, red skin color pattern, its tart-like flavor, taste and high dessert quality and otherwise as herein described.

3 Drawing Sheets

This application is a continuation of U.S. application Ser. No. 08/013,021 filed Feb. 2, 1993, now abandoned.

BACKGROUND AND SUMMARY OF INVENTION

This invention relates to a new and distinct variety of apple tree and more particularly to a spontaneous limb-sport mutation of the apple variety commonly known as Jonagold, a non-patented variety.

The discovery was made by the inventor, Mr. Romain Surkijn, in 1983, in one of his cultivated apple orchards located at Betserbaan 40, B-3460, Halen, Belgium.

The mutation appeared as a spontaneous limb-sport in the upper portion of a two (2) year old Jonagold tree (FIG. 1). The inventor (discoverer) was attracted to this new Jonagold sport by the early, broadly striped, bright, red coloring of its fruit (See FIGS. 3 and 5). The winter following this discovery, the inventor collected grafting wood from the sport-limb to use for grafting of second (2nd) generation trees and for topworking. Second (2nd) generation trees were grafted in the spring of 1985. The new cultivar was named "Romagold" for all future reference use (FIG. 2).

Several (6) trees were also top worked in order to speed up the production of second (2nd) generation fruit and to see if this new discovery was stable in the next generation. These grafts produced second (2nd) generation fruit the following fall (1986) and in all succeeding years. Third (3rd) generation fruits have now also been produced and all second (2nd) and third (3rd) generation fruit show the same early unique broadly striped red fruit coloration identical to fruits grown on the original sport limb.

The new Romagold variety has been carefully compared to its parent, the Jonagold variety (unpatented), and to other red Jonagold sport varieties now being grown, including Jonagored (U.S. Plant Pat. No. 5,937), Daliguy (U.S. Plant Pat. No. 6,148), Jonica (U.S. Plant Pat. No. 7,146), Rubinstar (U.S. Plant Pat. No. 7,590) and Jonagold De Coster (U.S. Plant Pat. No. 8,049).

Fruit skin color, shape, color intensity and other fruit characteristics of the new variety are compared in Table 1 to the varieties listed above, and are hereby further described:

1. The skin color of Romagold takes on a distinctive, and heavily striped pattern heavier and earlier than that of the parent tree, with the stripes being conspicuously a more prominent, darker red in appearance than those of the parent tree and the color sports within the market class. As the fruit advances to the stage of market ripeness, essentially the totality of the remaining unstriped surface of the fruit skin takes on a solid or block red blush, resulting in an essentially solid red apple which has subtle but definite deep red stripes over the attractive red ground color which, with the deep red stripes, covers 75% or more of the total fruit exterior. This results in a fruit which has an enhanced rich dark-red-over-red surface coloration which is frequently preferred by the fresh apple consumer.

2. The above mentioned broad red striped effect is particularly noticeable when Romagold fruit is displayed in packed cartons and or boxes. This color pattern differs distinctively from displays made up of blush (block) colored fruits. The value of this broad bright red striped characteristic is of considerable importance when marketing the fruit since striped red apple fruits are now preferred over blush (block) colored fruits in most world markets.

3. The value of this characteristic is also demonstrated in poor coloring years and in poor coloring apple growing districts. Poorly colored striped apples are always preferred over equally poorly colored solid-red (block) colored fruits.

When comparing Romagold to the other five patented red Jonagold varities the following fruit skin differences were noted:

1. Romagold's broadly striped bright red skin color was distinctive and markedly different from the more over-all solid block colored fruits of Jonagold De Coster, Jonagored and Rubinstar. The finished color of these three clones showed only very slight and/or no striping of fruit skin color at harvest.

2. The finished skin color of fruits of the Daliguy and Jonica varieties often showed a tomato red to dull brown red color characteristic at harvest. This differed distinctly from Romagold's very broad bright red chimera-like stripes.

3. Over-all fruit color percentages were difficult to measure because of the differing fruit coloring characteristics. See Table 1 for estimated percentages of overall red skin color at harvest of all Jonagold red sport varieties tested. However, the new Romagold variety exhibits many more chimera-like stripes than the other Jonagold red sport varieties, which tend to exhibit more of a blush (block) skin coloration.

ROMAGOLD COLOR COMPARISON TABLE #1

| | ROMAGOLD | JONAGOLD DE COSTER (USPP 8049) | JONAGORED (USPP 5937) |
|---|---|---|---|
| Early color development of fruit | Begins to color about two weeks ahead of Jonagold middle of August in Halen, Belgium. Begins to color with a heavy stripe pattern. | Similar to Standard Jonagold with some pink to red additional color visible from July through early September. | Brownish brown-red color throughout the growing season, darkening and reddening in early September. |
| Fruit finish color - shade | Overall glossy bright cherry red. Produces more red surface than Jonagored, colors well, even on shaded sides of fruit. (39–12 Munsell Color chart) | Very bright wine red tone similar to Standard Jonagold with no brown tones. Finish tone is between 818 Jasper red and 818 Orient red (RHCCL) | Dark red to brown red; 821 Currant red to 822 Cardinal red (RHCCL) |
| Finish fruit color - % | 75–100% bright cherry red with heavy broad stripes. | Many fruits with 85–95% red color, some light stripes. | Many fruits with 85–95% red color, some apples blush finish, others some stripes. |

| | RUBINSTAR (USPP 7590) | DALIGUY (USPP 6148) | JONICA (USPP 7146) |
|---|---|---|---|
| Early color development of fruit | Starts very early at the end of August in a brownish way. | Light green, dark green. | Light green. |
| Fruit finish color - shade | Transforms from brown into dark red. | Bright wine red with white to yellow background. | Brown to pink-red. |
| Finish fruit color - % | Many fruits with 90–100% block red color. | Many fruits with 30–40% red color stripes over a white to yellow background with more intensity than standard | Many fruit colors with 70% in a pink red. Others may stay brownish pink red. |

Romagold has growth characteristics similar to its parent and to the other five sport clones compared to it. All exhibit an open standard-type (non-spur) growth characteristic. (See Table 2).

ROMAGOLD TREE COMPARISON TABLE #2

| | ROMAGOLD | JONAGOLD DE COSTER (USPP 8049) | JONAGORED (USPP 5937) |
|---|---|---|---|
| Growth | upright, vigorous, | upright rather vigorous, | vigouous, non-spur |

-continued

ROMAGOLD TREE COMPARISON TABLE #2

| | | | |
|---|---|---|---|
| | non-spur | non-spur | |
| Bearing Habit | regular annual bearer | regular annual bearer | regular annual bearer |
| Trunk and Branches | medium stock, medium thick | moderately thick, no spur growth | moderately thick |
| Bark Color | dark grey | grey | dark grey |
| Vigor | same as standard | same as standard | grows 5–10% more than standard |
| Productivity | 100% | 100% | 90% |

| | RUBINSTAR (USPP 7590) | DALIGUY (USPP 6148) | JONICA (USPP 7146) |
|---|---|---|---|
| Growth | less upright, much less vigorous, non-spur | upright, less vigorous, non-spur | less upright, much less vigorous, non-spur |
| Bearing Habit | regular annual bearer | tendency to biannual bearing | regular annual bearer |
| Trunk and Branches | thin | moderately thick | thin |
| Bark Color | very dark grey | dark grey | grey |
| Vigor | virus infected, grows 10% less than standard | same as standard | VF grows 10% less than standard |
| Productivity | 80% | 90% | 80% |

Since Romagold possesses standard non-spur growth characteristics, a variety of tree training methods can be employed, such as:

1. Free standing central leader training with trees on either seedling or the more vigorous dwarfing rootstocks.

2. Central Axis training with either pole or wire support on dwarf type rootstocks.

3. Trellis-type training methods may be employed where more vigorous, non-spur type growth is necessary for proper training on dwarfing type rootstocks.

No noticeable differences have been observed in fruiting habits between Romagold and its parent Jonagold or the other five red Jonagold clones tested. Precocity and response to chemical thinning are similar.

No noticeable significant differences were recorded or observed in fruit size between all of the clones of red Jonagold. There are, however, a number of other differences between the fruit characteristics of the new Romagold variety and the red Jonagold clones, as shown and described in detail in Table 3.

ROMAGOLD FRUIT COMPARISON TABLE #3

| | ROMAGOLD | JONAGOLD DE COSTER (USPP 8049) | JONAGORED (USPP 5937) |
|---|---|---|---|
| Shape | large, uniform, round to slightly conical | not as large, more uniform in size, globose conical | very large, not uniform size, oblong conical |
| Stem | long | long | medium long |
| Calyx | partly open | quite shallow | shallow |
| Cavity | acute, medium deep | broad, medium deep | rather small, medium to shallow |
| Skin | smooth, glossy | smooth | smooth |
| Color at Harvest | almost 100% bright red broad strips, | uniform wine red background green to yellow | dark red to purple, little to no back- |

-continued

ROMAGOLD FRUIT COMPARISON TABLE #3

| | | | |
|---|---|---|---|
| | some chimeras (see Figs. 3 & 4) | when ripe, little striping, mostly solid block color appearance | ground striping, solid block color appearance |
| Lenticels | small, conspicuous, few & scattered at base | numerous | numerous |
| Calyx Tube | reflexed and divergent, broad funnel form | long narrow | long narrow |
| Core | median | small and round | small and round |
| Seeds | .5 to 1 cm wide obtuse, dark brown | large wide | large wide |
| Flesh | creamy white | white yellowish | yellowish |
| | RUBINSTAR (USPP 7590) | DALIGUY (USPP 6148) | JONICA (USPP 7146) |
| Shape | smaller, more uniform in size, flat globose | large, not uniform in size, globose conical | rather large, not uniform in size, flat globose |
| Stem | long | medium long | long |
| Calyx | quite shallow, some half open | shallow, some half open | shallow, closed |
| Cavity | broad, medium deep | broad, medium deep | small, medium to shallow |
| Skin Color at Harvest | very smooth uniform dark red with very little green background, solid block color appearance | smooth intense tomato red with a green to yellow background | very smooth dull brown red to pink red with green to yellow background |
| Lenticels | less | less | less |
| Calyx Tube | long narrow | not so long, narrow | short wide, not small and flat |
| Core | not small and flat | small and round | not small and flat |
| Seeds | very small and very thin | large wide | very large, very wide |
| Flesh | yellowish | yellowish | white yellowish |

As is common to many super-red sports of red apple cultivars, leaves of Romagold are a slightly darker green color when compared to leaves of its parent variety. The varieties were compared under similar growth conditions, i.e., pruning, nitrogen, water, etc. The difference in green color shade is too slight to determine on the color chart being used.

Similarly, compared to the Jonagold variety, the pinkish red color of some of the leaf petioles and midribs of Romagold are slightly more pronounced and intense than on the leaves of its parent variety. This pinkish-red color often extends further down the midrib.

No bark or tree growth differences have been noted. Surface bloom is formed on the skin of the fruit, but does not differ from surface bloom on other red Jonagold clones tested. Winter hardiness appears to be similar to its parent and the other red Jonagold clones tested. Spring blossom hardiness also appears to be similar. As with Jonagold and the other cultivars tested, the skin of Romagold has shown no russet problems.

The new Romagold variety is free of all 10 known viruses and virus-like diseases, and is resistant to the common fungal and bacterial diseases of apples.

THE DRAWINGS

The accompanying full-color pictures and tables illustrate the new Romagold apple tree and the characteristics of its fruit.

Figure 5:
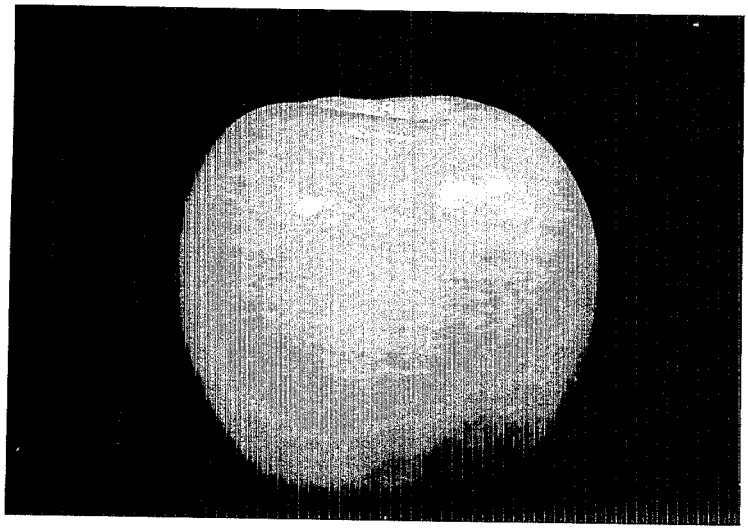

FIG. 5 Color photograph showing Romagold's broad, red stripes.

DESCRIPTION OF THE VARIETY

Following is a detailed description of the new variety with color terminology in accordance with the Munsell Color Cascade Chart except where general color terms of ordinary dictionary significance are used.

1. Parentage: A spontaneous limb-sport of the apple variety Jonagold (unpatented).
2. Locality where grown and observed:
   Halen, Belgium.
   Brogdale Experimental Horticultural Station.
   Faversham-Kent, England.
   Goren Research Station, Belgium.
   Yakima, Wash. U.S.A.
3. Dates of first and last pickings: About September 25 and October 10, respectively, in Halen, Belgium. About September 20 and October 1, respectively, in Yakima, Wash., U.S.A.
4. Tree: Medium large, vigorous, dense foliage, rapid grower, upright.
   *Trunk.*—Medium stocky, smooth, dark-brown (26-15).
   *Branches.*—Medium thick, smooth, stocky, green-brown (23-13).
   *Lenticels.*—Medium size, few, not raised, whitish-grey.
   *Twigs.*—Slender.
   *Color.*—Grey with reddish terminal buds.
5. Leaves: Large, long, medium wide, lanceolate, abruptly pointed, medium thick.
   *Length.*—Average 7.5 cm.
   *Width.*—Average 5.8 cm.
   *Color.*—Green to dark-green (19-13).
   *Margin.*—Moderately serrate.
   *Petiole.*—Medium long (3 cm to 3.5 cm), medium slender.
   *Pose.*—Upward.
   *Vein.*—Pink to red on back side of leaves.
6. Flowers:
   *Date of first and full bloom.*—About April 15 and April 25 respectively in Halen, Belgium. About April 10 and April 21, respectively, in Yakima, Wash., U.S.A.
   *Size.*—Medium large.
   *Overall color.*—Light red (43-8).
   *Pedicels.*—Red.
   *Sepals.*—Green with light-red tips.
   *Stamens.*—Dark red.
7. Fruit:
   *Maturity when described.*—Eating ripe. (Specimens described were grown and observed at Halen, Belgium, and at Yakima, Wash., U.S.A.

*Size.*—Large, uniform.
*Axial diameter.*—About 7.5 cm to 8.5 cm.
*Horizontal diameter.*—About 6.5 cm to 7.5 cm.
*Form.*—Regular, uniform, round to slightly conical, sides equal, rounded at base.
*Cavity.*—Acute, medium width, medium depth, symmetrical. reddish-green, very slight russet.
*Basin.*—Abrupt, symmetrical, five crowned, regular, medium width, medium depth.
*Markings.*—None.
*Stem.*—Long, slender (3 cm to 4 cm).
*Calyx.*—Partly open, calyx lobe persist and separate at base.
*Calyx lobes.*—Reflexed and divergent.
*Pubescence.*—Slight.

Figure 4:
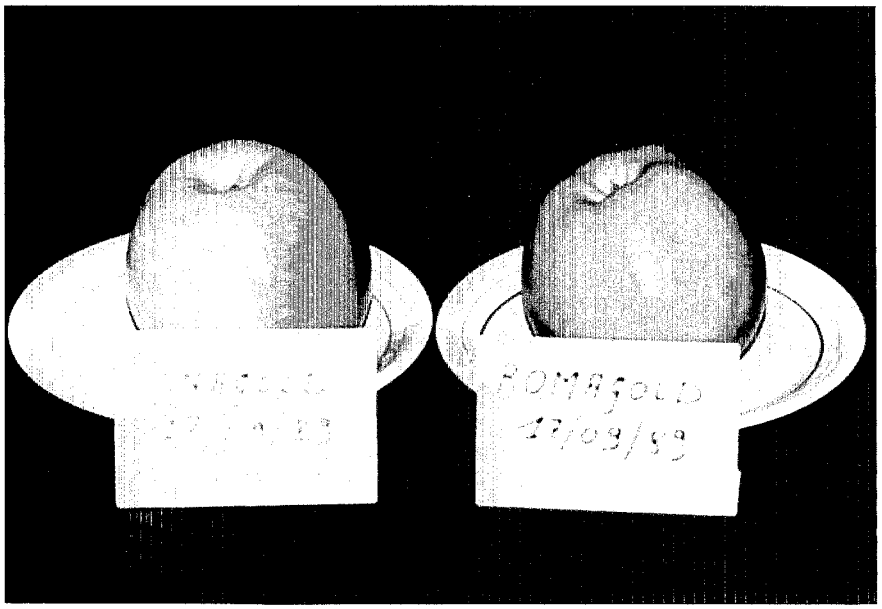
FIG. 4 Shows a color comparison—Romagold v. Jonagold at picking maturity.
Figure 3:
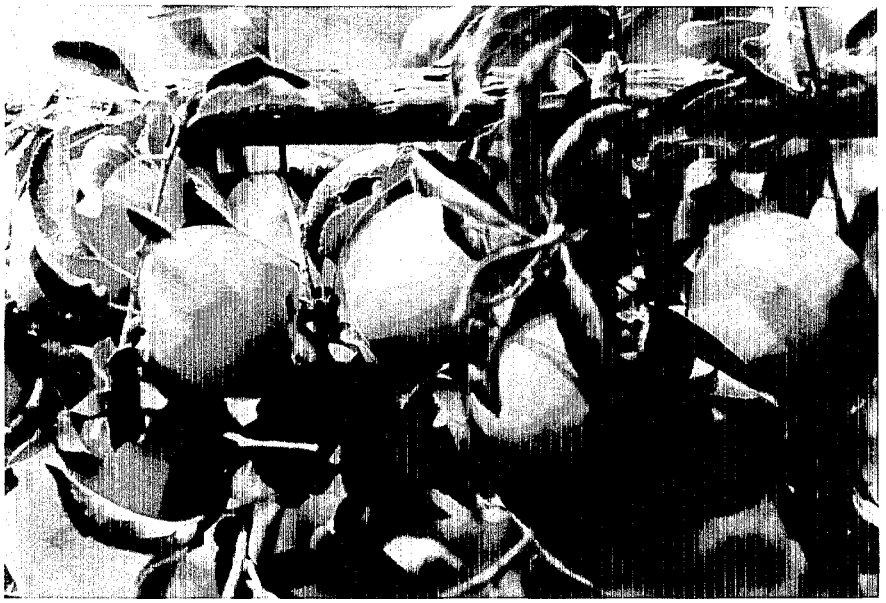
FIG. 3 Is a close-up view of Romagold fruit showing broad stripes and bright red skin color.

8. Skin: Smooth, glossy, medium thickness.
*Stem cavity.*—Reddish-green.
*Dot.*—Small, conspicuous, few and scattered at base. (FIG. 3).
*Suture.*—None.
*Color.*—Broad red chimera-like stripes, almost 100% bright red (39-12) (FIGS. 3 and 4).
*Flesh.*—Solid, juicy.
*Color.*—Creamy white.
*Texture.*—Firm, fine, crisp, tender.
*Flavor.*—Sweet to sub-acid.
*Aroma.*—Fruity, distinct.
*Quality.*—Best.

9. Core: Median.
*Bundle area.*—Symmetrical, medium small.
*Halves of area.*—Equal.
*Bundle.*—Inconspicuous.
*Core lines.*—Indistinct, meeting, broadly heartshaped.
*Cross section.*—Indistinct.
*Calyx tube.*—Broad funnel-form.
*Stem (cylinder) of funnel.*—Short to medium long.
*Depth of tube to shoulder.*—Less than 1 cm.
*Entire depth.*—About 2 to 2.5 cm.
*Style.*—Present, united at base.
*Stamen.*—Median, in one whorl.
*Seed cell (carpels).*—Open, axile, symmetrical, smooth, heart-shaped.

Figure 2:
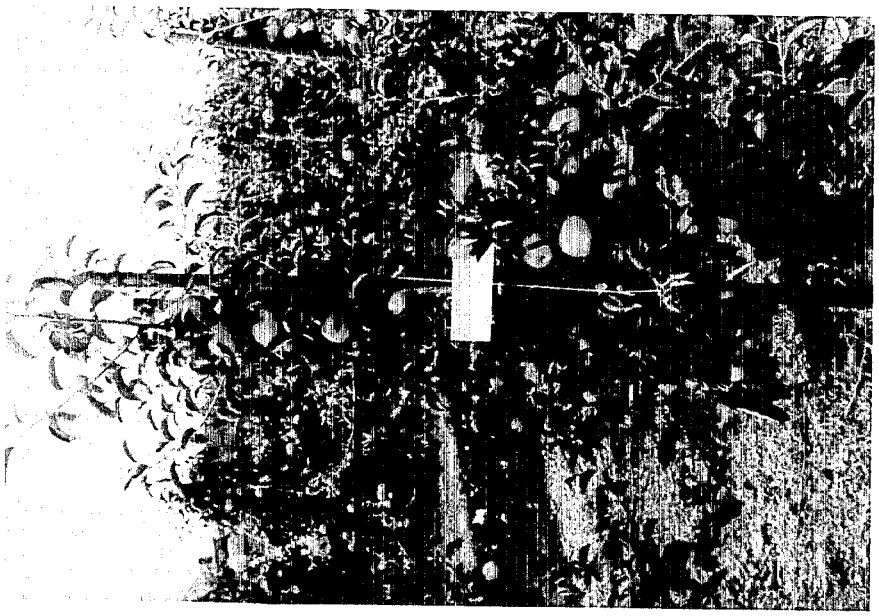
FIG. 2 Shows a three (3) year old second (2nd) generation tree of Romagold growing in the inventor's orchard near Halen, Belgium. Note standard Jonagold parent trees in background.
Figure 1:
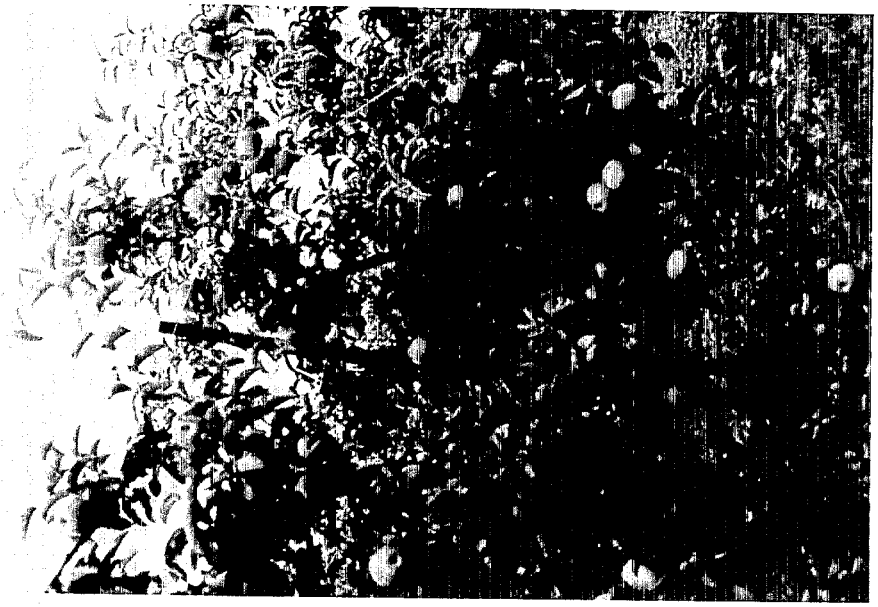
FIG. 1 Shows the sport limb on the original mother tree.

10. Seeds: One or two per cell, not tufted, acute at point, 1 to 1.5 cm long, 0.5 to 1 cm wide, obtuse, dark-brown (32-15).
11. Ploidy: Triploid.
12. Use: Dessert, juice, culinary, fresh market.
13. Keeping quality: Very good, up to 7 months in standard cold storage.
14. Resistance to insects and diseases: Average for scab and mildew. Virus-tested and virus free. Propagation wood available.
15. Winter hardiness: Hardy, same as parent variety.
16. Precosity: Similar to parent (FIG. 2).

I claim:

1. A new variety of apple tree substantially as herein shown and described, characterized particularly as to novelty by its early coloring red fruits which differ from fruits produced by its parent variety Jonagold and from all other known sport varieties of red Jonagold by their distinct broadly striped red color pattern which remains are harvest.

* * * * *